United States Patent [19]

Schmid et al.

[11] Patent Number: 5,677,273

[45] Date of Patent: Oct. 14, 1997

[54] WETTING AGENTS FOR THE PRETREATMENT OF TEXTILES

[76] Inventors: Karl-Heinz Schmid, Stifterstrasse 10, 40822 Mettmann; Ingo Wegener, Am Falder 133, 40589 Duesseldorf; Anja Hanke, Am Hoeschgrund 3, 47259 Duisburg; Michael Neuss, Sesamstrasse 2, 50997 Koeln; Hans-Christians Raths, Wiener-Neustaedter-Strasse 95, 40789 Monheim, all of Germany

[21] Appl. No.: 464,790

[22] PCT Filed: May 17, 1993

[86] PCT No.: PCT/EP93/01226

§ 371 Date: Jun. 22, 1995

§ 102(e) Date: Jun. 22, 1995

[87] PCT Pub. No.: WO94/14936

PCT Pub. Date: Jul. 7, 1994

[30] Foreign Application Priority Data

Dec. 22, 1992 [DE]  Germany ............................ 42 43 643.5

[51] Int. Cl.$^6$ ...................................................... C11D 1/722
[52] U.S. Cl. ........................... 510/356; 510/360; 510/421; 510/432; 510/506; 568/613
[58] Field of Search ........................ 252/174.21, 170, 252/162, 174.24, 174.19; 568/613; 510/356, 337, 340, 342, 351, 357, 360, 421, 422, 424, 427, 432, 477, 506

[56] References Cited

U.S. PATENT DOCUMENTS

| | | | |
|---|---|---|---|
| 2,520,611 | 12/1950 | Hoffman et al. | 260/615 |
| 2,626,243 | 5/1953 | Jacoby | 252/321 |
| 4,443,363 | 4/1984 | Klinger et al. | 252/547 |
| 4,624,803 | 11/1986 | Balzer et al. | 252/527 |
| 4,753,885 | 6/1988 | Dietsche et al. | 435/243 |
| 4,922,029 | 5/1990 | Birnbach et al. | 586/616 |
| 4,965,019 | 10/1990 | Schmid et al. | 252/321 |
| 5,059,342 | 10/1991 | Blease | 252/174.21 |
| 5,484,553 | 1/1996 | Guth et al. | 252/351 |

FOREIGN PATENT DOCUMENTS

| | | |
|---|---|---|
| 36550 | 9/1981 | European Pat. Off. . |
| 0124815 | 11/1984 | European Pat. Off. . |
| 0161537 | 11/1985 | European Pat. Off. . |
| 0180081 | 5/1986 | European Pat. Off. . |
| 0303928 | 2/1989 | European Pat. Off. . |
| 0324340 | 7/1989 | European Pat. Off. . |
| 0420802 | 12/1990 | European Pat. Off. . |
| 2800710 | 7/1979 | Germany . |
| 3744525 | 12/1988 | Germany . |

OTHER PUBLICATIONS

Piorr et al, "Low Foaming Biodegradable Nonionic Surfactants", Fat Sci. Technol. 89 106 (1987) No Month.
Tens.Surf.Det. 27, 243 (1990).
Fette, Seifen, Anstrichmitt., 87 421 (1985) No Month.

*Primary Examiner*—Paul Lieberman
*Assistant Examiner*—John R. Hardee
*Attorney, Agent, or Firm*—Ernest G. Szoke; Wayne C. Jaeschke; Real J. Grandmaison

[57] ABSTRACT

A wetting agent composition for pretreating textiles containing mixed ethers corresponding to formula I:

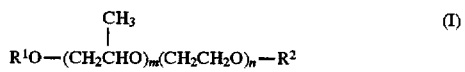

$$R^1O-(CH_2CHO)_m(CH_2CH_2O)_n-R^2 \quad \text{(I)}$$
with $CH_3$ branch wherein $R^1$ is a strictly linear alkyl radical containing from 8 to 10 carbon atoms, $R^2$ is an alkyl radical containing from 1 to 4 carbon atoms, m is a number from 0.5 to 2 and n is a number from 6 to 9.

11 Claims, No Drawings

WETTING AGENTS FOR THE PRETREATMENT OF TEXTILES

BACKGROUND OF THE INVENTION

1. Field of the Invention

This invention relates to wetting agents containing selected mixed ethers for the pretreatment of textiles and to the use of the mixed ethers for the production of wetting agents for the pretreatment of textiles.

2. Discussion of Related Art

Wetting agents are used in the pretreatment of yarns and fabrics, their function being for example to support the separation of impurities from the fibers or bleaching. Auxiliaries of this type are expected to satisfy a number of requirements. For example, they are required to be chemically stable under the often highly alkaline conditions, to have a wetting time of the order of a few seconds, to form no foam of their own, to suppress process foam and, in addition, to be readily biodegradable.

There are already many documents in the prior art which propose fatty alcohol polyglycol ethers and, more particularly, end-capped fatty alcohol polyglycol ethers, so-called "mixed ethers", as solutions to the problem for these and similar cases.

For example, EP-A 0 124 815 (Henkel) describes mixed ethers containing 8 to 18 carbon atoms in the fatty alkyl chain and 7 to 12 ethylene oxide units in the polyether chain as foam-inhibiting additives for low-foaming cleaning compositions. Octyl and/or decyl mixed ethers containing 3 to 4 ethylene oxide units are proposed for the same purpose in EP-B 0 303 928 (Henkel).

Mixed ethers containing 6 to 12 carbon atoms in the fatty alkyl group and EO/PO/EO blocks in the polyether chain are proposed in EP-A 0 180 081 (BASF) for the suppression of foam in the processing of foods and in fermentation processes. According to the teaching of EP-B 0 324 340 (Henkel), mixed ethers containing 6 to 28 carbon atoms in the fatty alkyl group and 2 to 10 ethylene oxide units in the polyether chain may be used for the same purpose.

Finally, EP-A 0 420 802 (Ciba-Geigy) describes wetting agents containing open-chain and/or end-capped fatty alcohol polyglycol ethers for the pretreatment of textiles. Suitable starting materials are said to include those which contain at least 8 and preferably 9 to 14 carbon atoms in the fatty alkyl group and 2 to 24 and preferably 4 to 8 alkylene oxide units in the polyether chain. They may be open-chain or end-capped by a $C_{1-8}$ alkyl group, a cycloaliphatic radical containing at least 5 carbon atoms and a lower phenyl or styryl group. The only Example refers solely to the use of an open-chain adduct of 15 moles of alkylene oxide with a $C_{9-11}$ oxoalcohol.

All these documents disclose a large number of possible mixed ether types and their advantageous use as foam regulators or wetting agents. However, none of them refers to the advantageous combination of the various parameters required or teaches the expert the criteria by which he has to combine the structural elements (fatty alkyl group, degree of propoxylation, degree of ethoxylation end capping) in order to obtain mixed ethers which satisfy the various requirements mentioned above.

Accordingly, the problem addressed by the present invention was to provide new wetting agents which, at one and the same time, would be low-foaming, foam-reducing, fast-wetting, alkali-resistant and readily biodegradable.

DESCRIPTION OF THE INVENTION

The present invention relates to wetting agents for the pretreatment of textiles containing mixed ethers corresponding to formula (I):

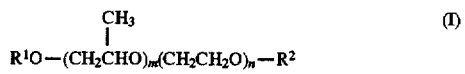

in which $R^1$ is a strictly linear alkyl radical containing 8 to 10 carbon atoms, $R^2$ is an alkyl radical containing 1 to 4 carbon atoms, m is a number of 0.5 to 2 and n is a number of 6 to 9.

It has surprisingly been found that, among the large number of mixed ethers known as low-foaming wetting agents, there is a limited range of species which eminently satisfy the requirements involved in the pretreatment of textiles, namely extremely low foaming, suppression of process foam, high wetting power, resistance to alkalis and excellent biodegradability. In addition, the products are highly stable in storage.

The following Examples and Comparison Examples show that even slight modification of the length of the fatty alkyl chain or the degree of ethoxylation is sufficient to produce a significant deterioration in wetting and foaming power whereas an increase in the propylene glycol content or the introduction of branchings into the fatty alkyl chain drastically diminishes the biodegradability of the products and their foam-suppressing effect.

Mixed ethers

Mixed ethers are known compounds which may be obtained by the relevant methods of preparative organic chemistry. They are normally produced by WILLIAMSON's ether synthesis in which fatty alcohol polyglycol ethers are condensed with alkyl halides in the presence of strong bases. Processes for their production are known, for example, from DE-OS 28 00 710 (Kuraray) and DE-C1 37 44 525 (Henkel). In addition, a review by Piorr et al. on the subject of mixed ethers can be found in *Fat Sci. Teohnol.* 1.89, 106 (1987).

Typical examples of mixed ethers which are suitable as constituents of the wetting agents according to the invention are methyl-, ethyl- or butyl-end-capped adducts of 0.5 to 2 moles of propylene oxide and 6 to 9 moles of ethylene oxide with octanol and/or decanol. Mixed ethers corresponding to formula (I), in which $R^1$ is an octyl radical, $R^2$ is an n-butyl radical, m is a number of 1.2 to 1.7 and n is a number of 6 to 8, more particularly 7 to 8, are preferred from the applicational point of view. A mixed ether obtainable by addition of first 1.2 moles of propylene oxide and then 6 or 7 moles of ethylene oxide onto octanol and subsequent end capping with butyl chloride is mentioned in particular with regard to low foaming, wetting power and biodegradability.

The expression "strictly linear" in the context of the invention is intended to mean that the content of branched species in the fatty alkyl chain should not exceed 0.5% by weight. It is clear from this that mixed ethers based on oxoalcohols, of which the percentage content of branched homologs is typically in the range from 5 to 25% by weight, are unsuitable for the wetting agents according to the invention.

The wetting agents according to the invention may contain the mixed ethers corresponding to formula (I) in quantities of 5 to 90% by weight and preferably 50 to 85% by weight, based on the wetting agent. In addition, the wetting agents according to the invention may contain other typical additives, more particularly hydrotropes and solvents.

Hydrotropes a1) Suitable hydrotropes are linear or branched, aliphatic alcohols containing 4 to 8 carbon atoms. Typical examples are ethanol, propanol, butanol, pentanol, caproic alcohol and 2-ethyl hexanol.

a2) Other suitable hydrotropes are cycloaliphatic alcohols of the terpenol type, such as for example geraniol, dihydroterpinol, nopol, myrcernol and terpineol.

a3) Other suitable hydrotropes are aromatic alcohols such as, for example, benzyl alcohol, phenyl ethanol, phenoxy ethanol, 1-phenoxy-2-propanol (phenoxy-isopropyl alcohol) and cinnamic alcohol.

a4) From the group of anionic surfactants, sulfonates of camphor, toluene, xylene, cumene and naphthol may be used. Other suitable anionic surfactants are sulfates of fatty alcohols containing 6 to 22 carbon atoms such as, for example, caproic alcohol, caprylic alcohol, 2-ethyl hexyl alcohol, capric alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol and erucyl alcohol and the technical mixtures thereof obtained, for example, in the hydrogenation of technical methyl ester fractions or aldehydes from Roelen's oxo synthesis. The surfactants may be used in the form of their alkali metal salts, more particularly sodium or potassium salts.

a5) Other suitable hydrotropes are dicarboxylic and polycarboxylic acids such as, for example, malonic acid, succinic acid, glutaric acid, adipic acid, pimelic acid, suberic acid, azelaic acid, sebacic acid, fumaric acid, maleic acid, tartaric acid, malic acid, citric acid and aconitic acid and also polyacrylic acids and alkyl phosphonic acids. The acid may be used in free form and also in the form of their alkali metal salts or partial esters.

a6) Other suitable hydrotropes are nonionic surfactants, more particularly adducts of, on average, 5 to 10 moles of ethylene oxide and fatty alcohols containing 6 to 18 carbon atoms which may have a conventional or narrow homolog distribution. Typical examples are adducts of 4 moles of ethylene oxide with octanol or 5 moles of ethylene oxide with decanol. Other suitable nonionic surfactants are, in particular, alkyl oligoglucosides and fatty acid-N-alkyl glucamides. Typical examples of compounds belonging to this class are $C_{12/14}$ cocoalkyl glucoside and lauric acid-N-methyl glucamide.

The percentage content of hydrotropes in the wetting agents according to the invention is typically from 1 to 25% by weight and preferably from 5 to 20% by weight.

Solvents

Typical examples are cyclohexanol, methyl cyclohexanol, tetralin and 3,5,5-trimethyl hexanol. Preferred solvents are apolar solvents which have a flash point above 65° C. Esters, such as tributyl citrate or tributyl phosphate for example, may also be used as apolar organic solvents. The percentage content of solvents in the wetting agents according to the invention is typically from 0 to 10% by weight and preferably from 2 to 8% by weight.

Wetting agents

The wetting agents according to the invention may be prepared by introduction of the mixed ethers and, optionally, the other ingredients into water. This involves a purely mechanical operation assisted by stirring and elevated temperature (30° to 40° C.); no chemical reaction is involved.

A typical wetting agent formulation has the following composition for example:

| | |
|---|---|
| Mixed ether (octanol 1.2 PO/6 EO butyl ether) | 30% by weight |
| 2-Ethyl hexyl sulfate, Na salt (30% by weight solution) | 10% by weight |
| Decyl alcohol 5 EO | 5% by weight |
| 3,5,5-Trimethyl hexanol | 5% by weight |
| Water | 5.0% by weight |

The quantity in which the wetting agents according to the invention are added to the treatment liquors may be between 1 and 10 g per liter of liquor and is preferably between 0.5 and 5 g per liter of liquor. The liquor may of course contain other additives, for example dyes, optical brighteners, alkalis, such as sodium hydroxide for example, sequestering agents, such as phosphonates and waterglass.

INDUSTRIAL APPLICATIONS

The wetting agents according to the invention are foam-free, fast-wetting, highly alkali-resistant, stable in storage and readily biodegradable. They suppress process foam and, accordingly, are suitable for the production of compositions for the pretreatment of textiles. By pretreatment is meant in particular the alkaline pretreatment and the chlorine and peroxide bleaching of raw cotton. However, pretreatment in the context of the invention is also understood to include the typical pretreatment (for example cleaning or dyeing from a bath) of fibers and fiber blends such as, for example, cellulose, wool, polyamide, polyacrylonitrile or polyester fiber materials and also polyacrylic/cotton and polyester/cotton blends.

The essence of the present invention lies in the inventive choice—not logical from the prior art—of short-chain mixed ethers with a strictly linear fatty alkyl chain and a low content of propylene and ethylene oxide units from the large number of mixed ethers already known for these or similar applications.

Accordingly, the present invention also relates to the use of mixed ethers corresponding to formula (I) for the production of wetting agents for the pretreatment of textiles in which they may be present in quantities of 5 to 90% by weight and preferably 50 to 85% by weight, based on the wetting agent.

The following Examples are intended to illustrate the invention without limiting it in any way.

EXAMPLES

Performance tests

Examples 1 to 10, Comparison Examples C1 to C9

1) Wetting power

Wetting power was determined by the immersion wetting method using 1 g of active substance/l, 20° C. in water with a hardness of 16° d. Particulars of this method can be found in *Tens. Surf. Det.* 27, 243 (1990). The wetting time $t_n$ in s was determined.

2) Foaming power

Foaming power was determined by the foam generation method using 1 g of active substance/l, 20° C., in water with a hardness of 16° d. Particulars of this method can be found in *Tens. Surf. Det.* 27, 243 (1990). The basic foam (t=0) and the foam collapse after 5 mins. in ml were determined.

3) Biodegradability

Biodegradability was assessed by the closed bottle test. The degradation rate BOD/COD after 30 days was determined against $C_{12/18}$ fatty alcohol 10 EO butyl ether (100%) as standard. Particulars of this test can be found in *Fette, Seifen, Anstrichmitt.*, 87 421 (1985). The results are set out in Table 1.

TABLE 1

Performance testing of mixed ethers

| Ex. | $R^1$ | $R^2$ | m | n | $t_n$ s | Foam (ml) 0' | Foam (ml) 5' | BOD/COD %-rel. |
|---|---|---|---|---|---|---|---|---|
| 1 | $C_8$ | $C_4$ | 1.2 | 7 | 20 | 0 | 0 | 107 |
| 2 | $C_8$ | $C_4$ | 1.2 | 8 | 18 | 0 | 0 | 107 |
| 3 | $C_8$ | $C_4$ | 1.2 | 9 | 19 | 0 | 0 | 106 |
| 4 | $C_8$ | $C_4$ | 1.5 | 8 | 18 | 0 | 0 | 105 |
| 5 | $C_8$ | $C_4$ | 1.7 | 8 | 18 | 0 | 0 | 101 |
| 6 | $C_{8/10}$* | $C_4$ | 1.2 | 7 | 22 | 0 | 0 | 107 |
| 7 | $C_{8/10}$ | $C_4$ | 1.2 | 8 | 21 | 0 | 0 | 107 |
| 8 | $C_{8/10}$ | $C_4$ | 1.2 | 9 | 21 | 0 | 0 | 107 |
| 9 | $C_{8/10}$ | $C_4$ | 1.5 | 8 | 21 | 0 | 0 | 105 |
| 10 | $C_{8/10}$ | $C_4$ | 1.7 | 9 | 21 | 0 | 0 | 100 |
| C1 | $C_8$ | $C_4$ | 1.2 | 4 | 23 | 50 | 40 | 103 |
| C2 | $C_8$ | $C_4$ | 1.2 | 5 | 23 | 30 | 20 | 102 |
| C3 | $C_8$ | $C_4$ | 1.2 | 6 | 26 | 40 | 30 | 99 |
| C4 | $C_8$ | $C_4$ | 1.2 | 10 | 28 | 50 | 40 | 97 |
| C5 | $C_{9/11}$# | $C_4$ | 1.2 | 8 | 20 | 30 | 20 | 89 |
| C6 | $C_{12/14}$+ | $C_4$ | 1.2 | 7 | 23 | 10 | 5 | 100 |
| C7 | $C_{12/14}$ | $C_4$ | 1.5 | 7 | 23 | 5 | 0 | 99 |
| C8 | $C_{12/14}$ | $C_4$ | 1.2 | 8 | 24 | 10 | 5 | 100 |
| C9 | $C_{12/14}$ | $C_4$ | 1.5 | 9 | 24 | 5 | 0 | 98 |

Legend:
*Basis $C_{8/10}$ head-fractionated fatty alcohol
Basis $C_{9/11}$ oxoalcohol (35% by weight branched components)
+Basis $C_{12/14}$ cocofatty alcohol Example 11, Comparison Examples C11 and C12

The foam-suppressing effect of the wetting agents was determined by the free-fall circuit method. The foaming of 1 g/l of Resolinrot was tested both on its own and with addition of 1 g/l of mixed ether. The test mixtures were heated from T =20 to 54° C. over a period t of 30 minutes. The results are set out in Table 2.

TABLE 2

Foam suppression of mixed ethers

| Ex. | $R^1$ | $R^2$ | m | n | t mins. | T °C. | Foam height ml |
|---|---|---|---|---|---|---|---|
| 11 | $C_8$ | $C_4$ | 1.2 | 6 | 0 | 20 | 100 |
|  |  |  |  |  | 1 | 21 | 100 |
|  |  |  |  |  | 5 | 26 | 90 |
|  |  |  |  |  | 10 | 31 | 80 |
|  |  |  |  |  | 20 | 44 | 80 |
|  |  |  |  |  | 30 | 54 | 80 |
| C11 | Without-mixed ether |  |  |  | 0 | 20 | 300 |
|  |  |  |  |  | 30 | 54 | 300 |
| C12 | $C_{9/11}$ | $C_4$ | 1.2 | 8 | 0 | 20 | 300 |
|  |  |  |  |  | 1 | 21 | 310 |
|  |  |  |  |  | 5 | 26 | 340 |
|  |  |  |  |  | 10 | 31 | 350 |
|  |  |  |  |  | 20 | 44 | 340 |
|  |  |  |  |  | 30 | 54 | 330 |

We claim:

1. A wetting agent composition for pretreating textiles comprising mixed ethers corresponding to formula I:

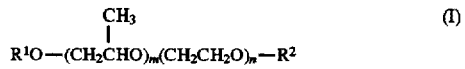

wherein $R^1$ is a strictly linear alkyl radial containing from 8 to 10 carbon atoms, $R^2$ is an alkyl radical containing 4 carbon atoms, m is a number from 1.2 to 2 and n is a number from 7 to 9.

2. A composition as in claim 1 wherein $R^1$ is an n-octyl radical, $R^2$ is an n-butyl radical, m is a number from 1.2 to 1.7 and n is a number from 7 to 8.

3. A composition as in claim 2 wherein said mixed ethers are present in an amount of from 5 to 90% by weight, based on the weight of said composition.

4. A composition as in claim 1 wherein said mixed ethers are present in an amount of from 5 to 90% by weight, based on the weight of said composition.

5. A wetting agent composition for pretreating textiles comprising mixed ethers corresponding to formula I:

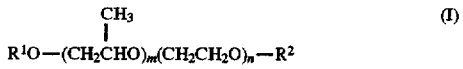

wherein $R^1$ is a strictly linear alkyl radical containing up to 0.5% by weight of branched species, based on the weight of $R^1$, and from 8 to 10 carbon atoms, $R^2$ is an alkyl radical containing to 4 carbon atoms, m is a number from 1.2 to 2 and n is a number from 7 to 9.

6. A wetting agent composition for pretreating textiles comprising:

(a) from 5 to 90% by weight of mixed ethers corresponding to formula I:

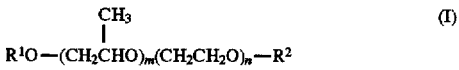

wherein $R^1$ is a strictly linear alkyl radical containing from 8 to 10 carbon atoms, $R^2$ is an alkyl radical containing 4 carbon atoms, m is a number from 1.2 to 2 and n is a number from 7 to 9; and (b) from 1 to 25% by weight of a hydrotrope selected from the group consisting of aliphatic alcohols containing 4 to 8 carbon atoms, terpineol cycloaliphatic alcohols, aromatic alcohols, anionic surfactants, dicarboxylic acids, polycarboxylic acids, nonionic surfactants, and mixtures thereof, all weights being based on the weight of said composition.

7. The composition of claim 6 wherein $R^1$ is an n-octyl radical, $R^2$ is an n-butyl radical, m is a number from 1.2 to 1.7 and n is a number from 7 to 8.

8. A wetting agent composition for pretreating textiles comprising:

(a) from 5 to 90% by weight of mixed ethers corresponding to formula I:

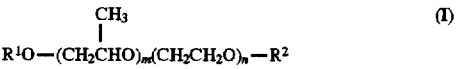

wherein $R^1$ is a strictly linear alkyl radical containing up to 0.5% by weight of branched species, based on the weight of $R^1$, and from 8 to 10 carbon atoms, $R^2$ is an alkyl radical containing 4 carbon atoms, m is a number from 1.2 to 2 and n is a number from 7 to 9; and (b) from 1 to 25% by weight of a hydrotrope selected from the group consisting of aliphatic alcohols containing 4 to 6 carbon atoms, terpineol cycloaliphatic alcohols, aromatic alcohols, anionic surfactants, dicarboxylic acids, polycarboxylic acids, nonionic surfactants, and mixtures thereof, all weights being based on the weight of said composition.

9. A process for pretreating textiles comprising contacting said textiles with a wetting agent composition, said composition comprising:

(a) from 5 to 90% by weight of mixed ethers corresponding to formula I:

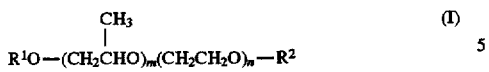

wherein $R^1$ is a strictly linear alkyl radical containing from 8 to 10 carbon atoms, $R^2$ is an alkyl radical containing 4 carbon atoms, m is a number from 1.2 to 2 and n is a number from 7 to 9; and (b) from 1 to 25% by weight of a hydrotrope selected from the group consisting of aliphatic alcohols containing 4 to 8 carbon atoms, terpineol cycloaliphatic alcohols, aromatic alcohols, anionic surfactants, dicarboxylic acids, polycarboxylic acids, nonionic surfactants, and mixtures thereof, all weights based on the weight of said composition.

10. The process of claim 9 wherein $R^1$ is an n-octyl radical, $R^2$ is an n-butyl radical, m is a number from 1.2 to 1.7 and n is a number from 7 to 8.

11. A process for pretreating textiles comprising contacting said textiles with a wetting agent composition, said composition comprising:

(a) from 5 to 90% by weight of mixed ethers corresponding to formula I:

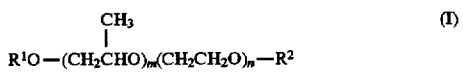

wherein $R^1$ is a strictly linear alkyl radical containing up to 0.5% by weight of branched species, based on the weight of $R^1$, and from 8 to 10 carbon atoms, $R^2$ is an alkyl radical containing 4 carbon atoms, m is a number from 1.2 to 2 and n is a number from 7 to 9; and (b) from 1 to 25% by weight of a hydrotrope selected from the group consisting of aliphatic alcohols containing 4 to 8 carbon atoms, terpineol cycloaliphatic alcohols, aromatic alcohols, anionic surfactants, dicarboxylic acids, polycarboxlic acids, nonionic surfactants, and mixtures thereof, all weights based on the weight of said composition.

* * * * *